(12) United States Patent
Scarr et al.

(10) Patent No.: US 10,127,349 B2
(45) Date of Patent: Nov. 13, 2018

(54) METHOD OF PRODUCING OLIGOMER AFFINITY PAIRS

(75) Inventors: Noah Scarr, Seattle, WA (US); Eugeny A. Lukhtanov, Bothell, WA (US)

(73) Assignee: ELITECHGROUP B.V., Spankeren (NL)

( * ) Notice: Subject to any disclaimer, the term of this patent is extended or adjusted under 35 U.S.C. 154(b) by 149 days.

(21) Appl. No.: 13/185,064

(22) Filed: Jul. 18, 2011

(65) Prior Publication Data

US 2012/0015358 A1    Jan. 19, 2012

Related U.S. Application Data

(60) Provisional application No. 61/365,219, filed on Jul. 16, 2010.

(51) Int. Cl.
*G06F 19/20* (2011.01)
*G06F 19/00* (2018.01)

(52) U.S. Cl.
CPC ................... *G06F 19/20* (2013.01)

(58) Field of Classification Search
None
See application file for complete search history.

(56) References Cited

U.S. PATENT DOCUMENTS 7,153,955 B2 * 12/2006 Miculka et al. ............. 536/26.9
2009/0017455 A1 * 1/2009 Kwong et al. .................... 435/6

OTHER PUBLICATIONS

Wu et al. (Bioinformatics, vol. 20, No. 11, 2004, pp. 1710-1717) (Year: 2004).*

European Patent Office; Invitation to Pay Additional Fees; PCT Application No. PCT/US2011/044375; Oct. 26, 2011.
European Patent Office; International Search Report and Written Opinion; PCT Application No. PCT/US2011/044375; dated Dec. 19, 2011.
Xu, Qikai, et al; Design of 240,000 Orthogonal 25mer DNA Barcode Probes; Proceedings of the National Academy of Sciences, vol. 106, No. 7, Feb. 17, 2009, pp. 2289-2294.
Gordon, Paul, et al; Osprey: A Comprehensive Tool Employing Novel Methods for the Design of Oligonucleotides for DNA Sequencing and Microarrays; Nucleic Acids Research, Oxford University Press, Surrey, GB, vol. 32, No. 17, Jan. 1, 2004, pp. e133.1-e133.9.
Li, Xingyuan, et al; Selection of Optimal Oligonucleotide Probes for Microarrays Using Multiple Criteria, Global Alignment and Parameter Estimation; Nucleic Acids Research, vol. 33, No. 19, Oct. 24, 2005, pp. 6114-6123.
Tanaka, F., et al; Design of Nucleic Acid Sequences for DNA Computing Based on a Thermodynamic Approach; Nucleic Acids Research, vol. 33, No. 3, Feb. 18, 2005, pp. 903-911.
The International Bureau of WIPO; International Preliminary Report on Patentability; PCT Application No. PCT/US2011/044375; Jan. 31, 2013.
European Patent Office; Response to Office Action; European Application No. 11736254.1; dated Sep. 24, 2013, 9 pages.
The Communication under Rule 164(2)(a) EPC issued by European Patent Office on Jul. 5, 2016 for the co-pending European patent application No. 11736254.1.

* cited by examiner

*Primary Examiner* — Pablo S Whaley
(74) *Attorney, Agent, or Firm* — Jackson Walker LLP

(57) ABSTRACT

The invention provides methods to identify pRNA- and pDNA oligomer affinity pairs. Affinity pairs comprised of nucleic acid oligomers which demonstrate no cross-reactivity ("orthogonal") are designed using software and empirically verified by thermodynamic study and lateral flow testing. The design software uses a semi-random algorithm to build such sequences of nucleic acid oligomers based on user-input parameters for affinity strength and orthogonal stringency. These pairs can be applied for use in multi-analyte solid support and lateral flow diagnostic tests.

12 Claims, 12 Drawing Sheets

Specification includes a Sequence Listing.

| Sequence ID | Name | Sequence (4'-2') |
|---|---|---|
| 1 | d9a8 | CTTCCATT |
| 2 | d9b8 | AATGGAAG |
| 3 | d10a8 | ATCACAGA |
| 4 | d10b8 | TCTGTGAT |
| 5 | d11a8 | GTTGAACT |
| 6 | d11b8 | AGTTCAAC |
| 7 | d12a8 | ATCTATCT |
| 8 | d12b8 | AGATAGAT |
| 9 | d13a8 | AACAAGAA |
| 10 | d13b8 | TTCTTGTT |
| 11 | d14a8 | TCTCTCAT |
| 12 | d14b8 | ATGAGAGA |
| 13 | d15a8 | TGTAGTCA |
| 14 | d15b8 | TGACTACA |
| 15 | d16a8 | GTTACTTA |
| 16 | d16b8 | TAAGTAAC |
| 17 | d17a9 | TTTTTTTC |
| 18 | d17b9 | GAAAAAAA |
| 19 | d18a8 | CAGATAGA |
| 20 | d18b8 | TCTATCTG |
| 21 | d19a8 | AGTGTGAT |
| 22 | d19b8 | ATCACACT |
| 23 | d20a8 | ACATCACA |
| 24 | d20b8 | TGTGATGT |
| 25 | d21a8 | TGATGTGA |
| 26 | d21b8 | TCACATCA |
| 27 | d22a8 | GTAAGTTG |
| 28 | d22b8 | CAACTTAC |
| 29 | d23a8 | CAAGAATC |
| 30 | d23b8 | GATTCTTG |
| 31 | d24a8 | GAACAAAC |
| 32 | d24b8 | GTTTGTTC |

Figure 2

Melting temperature analysis

| | d9a8 | d9b8 | d14a8 | d14b8 | d15a8 | d15b8 | d17a9 | d17b9 | d18a8 | d18b8 | d20a6 | d20b8 | d22a8 | d22b8 | d23a8 | d23b8 | d24a8 | d24b8 |
|---|---|---|---|---|---|---|---|---|---|---|---|---|---|---|---|---|---|---|
| d9a8 | ND | | | | | | | | | | | | | | | | | |
| d9b8 | 42 | ND | | | | | | | | | | | | | | | | |
| d14a8 | ND | 1 | ND | | | | | | | | | | | | | | | |
| d14b8 | 5 | 0 | 48 | -1 | | | | | | | | | | | | | | |
| d15a8 | ND | -1 | 2 | 3 | 7 | | | | | | | | | | | | | |
| d15b8 | -2 | 2 | 11 | 11 | 45 | 12 | | | | | | | | | | | | |
| d17a9 | ND | -2 | ND | 1 | 0 | 7 | ND | | | | | | | | | | | |
| d17b9 | 2 | 2 | 1 | 2 | 2 | 5 | 37 | 4 | | | | | | | | | | |
| d18a8 | 0 | 2 | 3 | 1 | 2 | 2 | 1 | 4 | 2 | | | | | | | | | |
| d18b8 | ND | 1 | ND | 16 | 2 | 7 | ND | 0 | 47 | ND | | | | | | | | |
| d20a8 | ND | 3 | -3 | -1 | -1 | -1 | -2 | 2 | 2 | 0 | 5 | | | | | | | |
| d20b8 | ND | ND | ND | 3 | 2 | 6 | ND | ND | 2 | ND | 39 | ND | | | | | | |
| d22a8 | 1 | -2 | -2 | ND | 4 | 0 | -1 | 0 | 2 | 1 | 0 | -1 | ND | | | | | |
| d22b8 | ND | 2 | ND | 0 | 3 | 2 | ND | 2 | ND | ND | ND | 0 | 39 | ND | | | | |
| d23a8 | ND | -1 | ND | ND | ND | ND | ND | ND | 0 | 0 | ND | -1 | -2 | 0 | ND | | | |
| d23b8 | ND | -2 | ND | 1 | 1 | 0 | ND | -4 | 0 | 0 | ND | ND | -1 | 0 | 41 | ND | | |
| d24a8 | ND | 0 | ND | -2 | 3 | ND | 2 | ND | 3 | ND | 0 | 6 | 1 | 1 | ND | 0 | ND | |
| d24b8 | ND | ND | ND | -1 | 3 | 1 | ND | 24 | 1 | ND | 0 | ND | 0 | -1 | -1 | -1 | 38 | ND |

ND = No Melting Transition Detected

Figure 3

| Biotinylated pDNAs for solution phase | | T20-tailed pDNAs for solid phase attachment | |
|---|---|---|---|
| d9a8-Bio | CTTCCATT-Biotin | d9b8-T20 | AATGGAAG-PEG-T20 |
| d14a8-Bio | TCTCTCAT-Biotin | d14b8-T20 | ATGAGAGA-PEG-T20 |
| d15a8-Bio | TGTAGTCA-Biotin | d15b8-T20 | TGACTACA-PEG-T20 |
| d17a9-Bio | TTTTTTTC-Biotin | d17b9-T20 | GAAAAAAA-PEG-T20 |
| d18a8-Bio | CAGATAGA-Biotin | d18b8-T20 | TCTATCTG-PEG-T20 |
| d20a8-Bio | ACATCACA-Biotin | d20b8-T20 | TGTGATGT-PEG-T20 |
| d22a8-Bio | GTAAGTTG-Biotin | d22b8-T20 | CAACTTAC-PEG-T20 |
| d23a8-Bio | CAAGAATC-Biotin | d23b8-T20 | GATTCTTG-PEG-T20 |
| d24a8-Bio | GAACAAAC-Biotin | d24b8-T20 | GTTTGTTC-PEG-T20 |

Figure 6

|   | 1 | 2 | 3 | 4 | 5 | 6 | 7 | 8 | 9 |
|---|---|---|---|---|---|---|---|---|---|
| # | Seq | | Comp | %GC | Setup Parameters | | | | |
| 1 | ATGTTCTA | | TAGAAACAT | 25 | Add to? | NO | | *x-check* | |
| 2 | CGTATTAA | | TTAATACG | 25 | # Sys | 12 | | | |
| 3 | GCATTTAA | | TTAAATGC | 25 | Length | 8 | | *run* | |
| 4 | TGCAATTA | | TAATTGCA | 25 | %GC, min | 20 | | | |
| 5 | TGTTTATG | | CATAAACA | 25 | %GC, max | 30 | | *clear* | |
| 6 | TACGTTTT | | AAAACGTA | 25 | Attempts | 100000 | | | |
| 7 | CTAGATTT | | AAATCTAG | 25 | Limbs | 1000 | | *clear limbs* | |
| 8 | CAAACTAA | | TTAGTTTG | 25 | Confirm | NO | | | |
| 9 | AACAACAA | | TTGTTGTT | 25 | Max m-in-a-row | 4 | | *help* | |
| 10 | AGATCATA | | TATGATCT | 25 | Min mismatch | 2 | | | |
| 11 | TTACACAT | | ATGTGTAA | 25 | Max GC-match | 2 | | *find max* | |
| | | | | | Min # sys | 5 | | | |
| | | | | | Count G-T | NO | | | |
| | | | | | Count G-A | YES | | | |
| | | | | | Comps on NC | YES | | | |

Figure 8

SEQUENCE LISTING

<160> NUMBER OF SEQ ID NOS: 7

<210> SEQ ID NO 1
<211> LENGTH: 38
<212> TYPE: DNA
<213> ORGANISM: Artificial Sequence
<220> FEATURE:
<223> OTHER INFORMATION: isothermal SDA primer L1

<400> SEQUENCE: 1
gcattatagt acctgtctcc tcagcactga gatcccct                              38

<210> SEQ ID NO 2
<211> LENGTH: 43
<212> TYPE: DNA
<213> ORGANISM: Artificial Sequence
<220> FEATURE:
<223> OTHER INFORMATION: isothermal SDA primer 6a6-E001
<220> FEATURE:
<221> NAME/KEY: misc_feature
<222> LOCATION: (1)..(1)
<223> OTHER INFORMATION: Pyranosyl ribonucleic acid (pRNA) cytosine
      analogue
<220> FEATURE:
<221> NAME/KEY: misc_feature
<222> LOCATION: (2)..(2)
<223> OTHER INFORMATION: Pyranosyl ribonucleic acid (pRNA) adenine
      analogue
<220> FEATURE:
<221> NAME/KEY: misc_feature
<222> LOCATION: (3)..(3)
<223> OTHER INFORMATION: Pyranosyl ribonucleic acid (pRNA) guanine
      analogue
<220> FEATURE:
<221> NAME/KEY: misc_feature
<222> LOCATION: (4)..(4)
<223> OTHER INFORMATION: Pyranosyl ribonucleic acid (pRNA) thymine
      analogue
<220> FEATURE:
<221> NAME/KEY: misc_feature
<222> LOCATION: (5)..(5)
<223> OTHER INFORMATION: Pyranosyl ribonucleic acid (pRNA) adenine
      analogue
<220> FEATURE:
<221> NAME/KEY: misc_feature
<222> LOCATION: (6)..(6)
<223> OTHER INFORMATION: Pyranosyl ribonucleic acid (pRNA) guanine
      analogue
<220> FEATURE:
<221> NAME/KEY: misc_feature
<222> LOCATION: (6)..(6)
<223> OTHER INFORMATION: Pyranosyl ribonucleic acid (pRNA) guanine
      analogue is conjugated to 9-O-Dimethoxytrityl-triethylene
      glycol,1-[(2-cyanoethyl)-(N,N-diisopropyl)]-phosphoramidite
      (Spacer 9, Glen Research)
<220> FEATURE:
<221> NAME/KEY: misc_feature
<222> LOCATION: (7)..(7)
<223> OTHER INFORMATION: n is t conjugated to 9-O-Dimethoxytrityl-
      triethylene glycol,1-[(2-cyanoethyl)-(N,N-diisopropyl)]-
      phosphoramidite (Spacer 9, Glen Research)

<400> SEQUENCE: 2
nnnnnnntga atagtcggtt acttcctcag cgcgtactcg acc                        43

<210> SEQ ID NO 3
<211> LENGTH: 13
<212> TYPE: DNA
<213> ORGANISM: Artificial Sequence
<220> FEATURE:
<223> OTHER INFORMATION: isothermal SDA Forward Bumper Primer 1

<400> SEQUENCE: 3

```
cgctgaaccg gat                                                      13

<210> SEQ ID NO 4
<211> LENGTH: 13
<212> TYPE: DNA
<213> ORGANISM: Artificial Sequence
<220> FEATURE:
<223> OTHER INFORMATION: isothermal SDA Reverse Bumper Primer 1

<400> SEQUENCE: 4
tggacccgcc aac                                                      13

<210> SEQ ID NO 5
<211> LENGTH: 11
<212> TYPE: DNA
<213> ORGANISM: Artificial Sequence
<220> FEATURE:
<223> OTHER INFORMATION: detection probe MTB GG1
<220> FEATURE:
<221> NAME/KEY: misc_feature
<222> LOCATION: (6)..(6)
<223> OTHER INFORMATION: super A base
<220> FEATURE:
<221> NAME/KEY: misc_feature
<222> LOCATION: (11)..(11)
<223> OTHER INFORMATION: n is g conjugated to Endo IV linker

<400> SEQUENCE: 5
tccgtntggt n                                                        11

<210> SEQ ID NO 6
<211> LENGTH: 13
<212> TYPE: DNA
<213> ORGANISM: Artificial Sequence
<220> FEATURE:
<223> OTHER INFORMATION: NALF Probe 1

<400> SEQUENCE: 6
atggtggata acg                                                      13

<210> SEQ ID NO 7
<211> LENGTH: 14
<212> TYPE: DNA
<213> ORGANISM: Artificial Sequence
<220> FEATURE:
<223> OTHER INFORMATION: NALF Probe 2
<220> FEATURE:
<221> NAME/KEY: misc_feature
<222> LOCATION: (14)..(14)
<223> OTHER INFORMATION: Super T base

<400> SEQUENCE: 7
gtggataacg tctn                                                     14
```

METHOD OF PRODUCING OLIGOMER AFFINITY PAIRS

This application claims priority to U.S. Provisional Patent Application Ser. No. 61/365,219, filed on Jul. 16, 2010, entitled ORTHOGONAL NUCLEIC ACID AFFINITY PAIRS, the entire content of which is hereby incorporated by reference.

FIELD OF THE INVENTION

The present invention relates to oligomer affinity pairs which may be used for solid phase-based tests and methods of producing oligomer affinity pairs. The invention relates to oligomer affinity pairs lacking non-specific cross-interaction which are suitable for multi-analyte tests.

BACKGROUND

In the field of point-of-care clinical chemistry, many test devices utilize direct protein-analyte affinity to express positive results for such analytes; for example protein analysis, drug screening, and medical diagnostics, among others (Camarero, 2008). In the case of lateral flow devices, a variety of proteins may be fixed on a membrane and when an analyte-containing sample flows over a specific protein for which the analyte has affinity, binding is effected. Additionally, a label is used, typically adhered to the analyte, to effect signal generation for interpretation of positive results.

Increased sensitivity can be achieved by mixing in solution the analyte and analyte-specific protein before subjecting the sample to lateral flow. Analyte to protein binding can be more complete when pre-mixing is used due to the additional binding time and better availability of protein binding sites in the absence of the constraints provided by a membrane. When analyte and protein are pre-mixed and already bound, a subsequent capture of protein-analyte on a membrane is required. Nucleic acid oligomer affinity pairs represent one method of capture wherein one half of the pair is bound to the protein and the corresponding complementary oligomer is bound to the membrane. Affinity ligand pairs have been used in various applications, including multiple sectors of life sciences across a range of pharmaceutical, biochemical, biophysical and diagnostic applications (Laitinen et al., 2006). Several types of affinity ligand pairs are being used to different extents: antibodies and their fragments; receptors and their ligands; avidin/biotin systems; textile and biomimetic dyes; (oligo)peptides; antisense peptides; chelated metal cations; lectins and phenylboronates; protein A and G; calmodulin; DNA; sequence-specific DNA; (oligo)nucleotides; heparin; and digoxigenin. (Labrou and Clonis, 1994; Hart and Basu, 2009). The importance of site-specific immobilization of proteins on solid supports in diagnostics has been reviewed (Carmerero, 2008).

While a single affinity pair of nucleic acid oligomers can be designed to function as a capture system on solid support or lateral flow, the design of larger numbers of affinity pairs for use in the same assay requires careful attention to avoid cross-interaction of non-specific pairs. In general, longer oligomers are more likely to contain cross-interacting subsequences which can adversely affect assay specificity. Short oligomers are therefore preferable to avoid such cross-interactions. Lateral flow immunoassays, nucleic acid lateral flow immunoassays (NALFIA), and nucleic acid lateral flow assays (NALF) have been reviewed (Postuma-Trumpie et al., 2009, this publication is hereby incorporated herein by reference in its entirety).

Because short natural DNA and RNA nucleic acid oligomers have relatively weak binding, alternate forms of nucleic acids with stronger binding characteristics are preferable. Examples include locked nucleic acid (LNA) and chimera LNA/DNA polymers, which demonstrate fast second-order kinetics with increased stability when hybridized to DNA targets (Christensen et al, 2001). The thermodynamic nearest neighbor parameters for LNA bases allow the $T_m$ prediction of LNA:DNA and chimera-LNA-DNA:DNA duplexes (McTigue et al., 2004). Pyranosyl nucleic acid (pRNA), and 3-deoxypyranosyl nucleic acid (pDNA) are polymers that preferentially pair with complementary pRNA or pDNA versus natural RNA and DNA sequences (Schlonvogt et al. 1996; U.S. Pat. No. 7,153,955). Pentopyranosyl nucleic acid preparation and use for the production of a therapeutic, diagnostic and/or electronic component has been described (U.S. Pat. No. 6,506,896). These pRNA and pDNA nucleic acids also exhibit faster binding kinetics versus natural DNA which presents advantages when running an assay which requires binding in a mobile environment.

The design of multiple nucleic acid sequences with the same $T_m$ poses special challenges for use in applications such as microarrays and nano-fabrications. It is essential to prevent undesired hybridizations. It is required that multiple nucleic acid sequences need to be designed that do not hybridize non-specifically with each other (Tanaka et al., 2005).

The $T_m$, of 6-mer oligomers were compared in Table 3 where it was shown that pRNA and pDNA respectively have $T_m$s of 41.4° C. and 31.2° C. in a buffer containing NaCl and $MgCl_2$. In comparison the $T_m$ of a corresponding DNA oligomer is 5.5° C. (calculated using MGB Eclipse™ Design Software 2.0. Epoch Biosciences, Bothell, Wash.) demonstrating the dramatically increased stability of the pRNA and pDNA duplexes. It was experimentally observed that an increased non-specific hybridization between multiple designed oligomers occurred as duplex stability increased (larger $T_m$s).

The problem of designing a system composed of nucleic acid pairs which exhibit orthogonality (the lack of cross reactivity with non-complementary pairs) is addressed in the present application and by the present invention. The inherent ability of nucleic acids to cross-pair among non-complementary strands, despite multiple mismatches, is effectively enhanced in nucleic acid systems such as pRNA and pDNA which exhibit stronger pairing per nucleotide versus natural DNA or RNA. Because empirical testing of $4^n$ oligomers (where n represents oligo length) is cumbersome and impractical, rules were applied in a design algorithm which limits the output of orthogonal pairs. As noted in the literature, random design of DNA 25-mers resulted in 10 million oligomers (Xu et al., 2009) which were culled using stability and potential cross-reactivity. The present application describes how application of stability and potential cross-reactivity rules to the design process results in an algorithm which greatly improves efficiency in generating such orthogonal nucleic acid pairs.

Site specific immobilization of proteins to solid supports is of great importance in numerous applications including medical diagnostics, drug screening and protein analysis, among others (Camerio, 2007). Köhn (2009) reviewed approaches for site specific immobilization. Chen et al., (2011) reported that, despite the tremendous progress in developing bioorthogonal chemistry for site-specific labeling and surface immobilization of proteins over the past decade, the demand for new bioorthogonal methods with improved kinetics and selectivities remains high.

The orthogonal pDNA ligand pairs described in the present application are ideally suited to site-specifically immobilize proteins and peptides to solid surfaces in a similar fashion as illustrated in FIG. 12. Bioconjugation techniques are well known in the art (Hermanson, 1996). As illustrated in FIG. 12, one partner of an affinity pair can be covalently attached to a solid support with known chemistries or through a polymer in a site-specific fashion. The complementary partner of the affinity pair can be covalently attached to a protein or peptide. The solid phase immobilized affinity ligand efficiently captures the affinity ligand-modified protein or peptide. The capture protein or peptide can then be used in variety of biological assays as immunosensors (Shen Z et al., 2008), diagnostic immuno assays, protein:protein base screening (Tomizaki et al., 2010) and protein drug screening (Maynard et al., 2009).

Detection of ligand captured targets is achieved by using numerous available detection reagents such as fluorescent- and colored-dyes, fluorescent- and colored-beads, nanoparticles, enzymes and the like. Oligomer affinity pairs disclosed in this application are ideally suited to prepare detection reagents to detect capture targets which include nucleic acids, proteins, peptides and small molecules. A similar approach to the one described in Example 3 can be used or alternatively the ligand recognizing the target can be derivatized with a pDNA affinity pair member as taught in the art (Hermanson 1996, pages 639-67) while the complementary affinity pair member is covalently attached to a detection moiety which may include fluorophores, fluorescent beads, colored beads, nanoparticles, enzymes and the like, each containing a reactive group for covalent attachment. Affinity pairs are ideal in instances where more than one detection moiety is required. The detection of influenza A, influenza B and respiratory syncytial virus with nanoparticle is reported in respiratory samples (Jannetto et al., 2010).

SUMMARY

The invention provides methods for identifying oligomer affinity pairs suitable for use in diagnostic assays. The identification of oligomer affinity pairs is facilitated by a software program which executes a method to design nucleic acid oligomer sequences. The oligomer affinity pair sequences may include pDNA or pRNA sequences, and are designed to provide multiple affinity pairs which lack cross-reactivity among the non-specific pairs. The affinity pairs of nucleic acid oligomers may be used in multi-analyte solid phase-based and lateral flow tests which require a high degree of specificity to avoid false positives.

The methods of the present invention include user-controlled variables which dictate the properties of the resulting affinity pairs, such as the number of pairs generated, stability, and stringency of non-cross-interaction. The software interprets the user-controlled variables and uses a semi-random algorithm to generate sequences satisfying the user's constraints. As the program successively builds each sequence by adding a randomly generated nucleic acid monomer, the sequence is checked for compliance. If the sequence is within the parameters of the user-controlled variables, the successive addition of random nucleic acid monomer is continued until the desired length (stability) is reached. If the sequence fails the parameters of the user-controlled variables, the program replaces the previously added nucleic acid monomer with a different monomer until compliance is reached or all possible monomers have been attempted.

In order to predict non-specific cross-interactions, oligomers generated are analyzed by frame-shifting all possible alignments of relevant oligomers. Each frame shift is analyzed to determine how many base-matches are present and whether the number of matches satisfies the user-controlled stringency parameters.

To expedite the design process, the method learns which sequences fail the user-controlled variable parameters and compares each newly generated sequence or subsequence against this database of failed sequences. If the sequence has already been demonstrated as a failure, the program designs alternative sequences. Once all possible sequences have been attempted the program ceases to attempt to design more sequences for the current set of affinity pairs.

Because one intended use of the affinity pairs is for lateral flow tests, the software program contains a user-controlled option which allows any membrane-bound oligomers' cross-interactions to be ignored. This is justified because the oligomers are bound to a membrane and may be spatially separated to make any cross-interactions among these particular oligomers irrelevant. Note, however, that membrane-bound oligomers are still interacting with non-membrane-bound ("capture") oligomers, therefore these interactions are still subjected to the user's stringency constraints.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2 illustrates an example of a software-generated set of orthogonal pDNA pairs. In each pair (distinguished by the first number) b strand is a complement to the a strand. Gray-shaded sequences were eliminated after melting temperature analysis;

FIG. 3 illustrates a melting temperature data matrix for all possible self- and cross-interactions for a selected set of pDNA sequences. The $T_m$ of each of the complementary pairs is shown in bold. A method for $T_m$ determination is shown in Example 1;

FIG. 6 illustrates sequences and structures of pDNA oligonucleotides used in the lateral flow test, namely biotin-pDNAs and their complementary $T_{20}$-PEG-pDNAs. In the latter chimeric oligomer, the pDNA is coupled through a polyethylene glycol linker to the $T_{20}$ DNA oligomer. These oligomers were used in FIG. 7 to identify cross-interaction polymers;

FIG. 8 illustrates a software output and the parameter list used to generate the output;

DETAILED DESCRIPTION OF PREFERRED EMBODIMENTS

Figure 1:
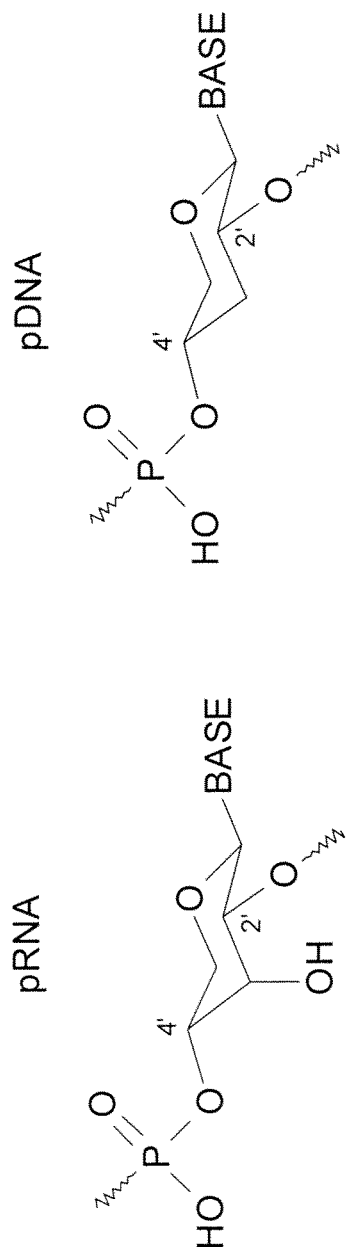
FIG. 1 shows a single polymeric unit of pRNA and pDNA emphasizing the sugar-phosphate backbones.

The present invention relates to oligomer affinity pairs suitable for solid phase-based tests and methods of producing affinity pairs. In one embodiment, the invention comprises a method for designing oligomer affinity pairs lacking non-specific cross-interaction which are suitable for multi-analyte tests which may or may not require spatially separate zones for each analyte. The invention further comprises specific oligomer affinity pairs for use in multi-analyte lateral flow tests.

Definitions

The term "chimeric oligomer" or "chimera" refers to an oligomer that comprises at least two sequences, each sequence consisting of a different type of nucleic acid. For example, a chimeric oligomer may comprise DNA and pDNA, DNA and pRNA, pDNA and pRNA, RNA and pDNA, RNA and pRNA, or any combination of pRNA and pDNA with either DNA or RNA. In some embodiments a chimeric oligomer has a structure X-(L)$_s$-Y, wherein s=0 or 1, L is a linking group compatible with oligonucleotide synthesis, and X and Y are independently pRNA, pDNA, DNA, RNA, LNA (lock nucleic acids) or PNA (peptide nucleic acids). In some embodiments the DNA and RNA contain one or more modified bases that hybridize to DNA and RNA but not to pDNA and pRNA. Modified bases have been disclosed in U.S. Pat. Nos. 6,485,906 and 7,045,610 which are incorporated by reference in their totality.

The term "affinity pair" refers to a set of molecules which bind to one another with a relatively higher affinity than to other molecules in an assay system. "Oligomer affinity pairs" refer to oligomers of RNA, DNA, pRNA, or pDNA, which bind to one another with a relatively higher affinity than to other molecules in an assay system. Oligomer affinity pairs may be partially or totally complementary in sequence. Members of an affinity pair may consist of the same nucleic acid as one another, or a different nucleic acid. One or more members of an oligomer affinity pair may be a chimeric oligomer.

The term "3'-deoxypyranosyl nucleic acid" or "pDNA" refers to a polymer that forms a pairing system which is orthogonal to naturally occurring DNA or other naturally occurring nucleic acids. pDNA preferentially hybridizes with complementary pRNA or pDNA versus natural DNA or RNA.

The term "pyranosyl nucleic acid" or "pRNA" refers to a polymer that forms a pairing system which is orthogonal to naturally occurring RNA or other naturally occurring nucleic acids. pRNA preferentially hybridizes with complementary pRNA or pDNA versus natural DNA or RNA.

The term "lateral flow testing" refers to assay systems which involve the movement of a fluid over an immobile surface, wherein the fluid may contain an analyte and the immobile surface includes a surface capable of preferentially binding the analyte. Lateral flow testing may include lateral flow immunoassays, nucleic acid lateral flow immunoassays (NALFIA), and nucleic acid lateral flow assays (NALF), as well as other types of assays known in the art.

The term "solid support" refers to a solid surface that can be used in diagnostic assays, including microfluidic channels, microspheres, magnetic beads, color beads, microarrays, microtiterplates, microchips, filters support, nylon-, gold-, polystyrene-surfaces, nanoparticles and the like.

Method for Generating Sets of Affinity Pairs

In one embodiment, the present invention comprises an algorithm for generating sets of affinity pairs which avoid non-specific cross-interaction. The affinity pairs may be nucleic acid oligomers. In some embodiments, the invention further comprises functional testing for non-specific cross-interactions after affinity pair candidates have been generated using the algorithm.

In an embodiment of the invention, user-controlled variables are defined, for example by querying a user and acquiring parameters from a user for one or more of the user-controlled variables. The user-controlled variables are then defined in the algorithm according to user input. The user-defined variables may include parameters relating to the stability of matched affinity pairs, such as 1) length, 2) % G-C minimum, and 3) % G-C maximum. The user-defined variable may also include parameters relating to the stringency for non-specific cross-interactions, such as 1) Count G-A as match, 2) Count G-T as match, 3) Maximum Matches in a Row, 4) Maximum Number of G-C Matches within Maximum Matches in a Row, and 5) Minimum Number of Mismatches between Two or More Maximum Matches in a Row.

In an embodiment of the invention, the user-controlled variables also include a parameter describing whether or not the affinity pairs are designed for immobilization on a solid support. If this variable is TRUE, the design algorithm ignores the cross-interactions among those oligomers arbitrarily bound to the membrane.

In an embodiment of the invention, the user-controlled variables also include a parameter describing a user-specified length for the oligomers. The user-specified lengths of the oligomers in an oligomer affinity pair may be the equal or unequal.

In an embodiment of the invention, a "violates parameters list" or "VP list" is assembled by the algorithm. A new VP list is initiated for each set of affinity pairs generated, and the algorithm refers any sequence which is inconsistent with the user-controlled variables to the VP list. The VP list represents a semi-random approach to generating candidate sequences which may be more efficient than random sequence generation.

In a further embodiment, the algorithm includes a step for evaluating whether the addition of a base causes the sequence to be in violation of the user-controlled parameters. If the addition of a base causes the sequence to be in violation of the user-controlled parameters, the program removes that base and randomly selects a different base to continue generating the sequence.

In a further embodiment, the method includes a step for allowing promiscuity of base-pairing in the oligomer affinity pair outside of Watson Crick pairing rules. The promiscuity can be recognized as a base match or ignored. Ignoring non-Watson-Crick base pairs loosens the design parameters to generate a larger set of affinity pairs at the expense of possible cross-interactions among non-complementary sequences.

Exemplary Methods

In one embodiment, the invention comprises a method which includes the following steps:

I) Generate a first sequence conforming to user-controlled parameters using the following steps:
   A) Randomize a first base to initiate a sequence;
   B) Analyze the first sequence to see if it is listed in the VP list:
     if the sequence is not listed in the VP list, then continue to I.C;
     if the sequence is listed in the VP list, then remove the most recently added base and add a different random base and return to I.B;
     if all possible bases have been added, the subsequence is also added to the VP list, then return to I.A;
   C) Analyze the sequence for user-defined variables:
     if the sequence does not violate the user-defined variable parameters, then continue to I.D;
     if the sequence violates the user-defined variable parameters, add the sequence to the VP list, then remove the most recently added base and add a different random base and return to I.B;
     if all possible bases have been added, the subsequence is also added to the VP list, then return to I.A;
   D) Generate a complement to the sequence, and analyze the complement to see if it is listed in the VP list:
     if the complement is not listed in the VP list, then continue to I.E;
     if the complement is listed in the VP list, return to I.A;
   E) Analyze the complement for user-defined variables:
     if the complement does not violate the user-defined variable parameters, then continue to I.F;
     if the complement does violate the user-defined variable parameters, add the sequence and the complement to the VP list and return to I.A;
   F) Extend sequences:
     if the user-specified length for oligomers has not been reached, add another random base to the first sequence and go to I.B
     if the user-specified length for oligomers has been reached, go to Section II.

II) Generate additional sequences conforming to the user-defined variable parameters, which do not cross-react with the sequence of Section I using the following steps:
   A) Following the procedure in Section 1, generate additional sequences using the same VP list used in Section I;
     1) If the user-controlled variable describing whether or not the affinity pairs are designed for immobilization on a solid support is TRUE, ignore the interactions of those oligomers which are arbitrarily designated as being bound to a solid support in Section I.C;
   B) If sequences pass both self-complement analysis as well as the VP list generated for the first sequence and any subsequent sequences, output the resulting sequences.

In one embodiment, the invention comprises a method which includes the following steps:

I) Load user-controlled variable parameters;
II) Generate the first sequence (and complement) conforming to the parameters in Section I using the following steps:
   A) Randomize the first base
   B) Analyze the sequence to see if it's in an existing set of sequences violating parameters in Section I (the "Violating Parameters," or "VP" list); if not, then continue to II.C; if it has been previously determined the sequence is not allowed, then remove the last added base and add another random base
     1) If analysis in II.B shows the sequence to be violating parameters and all possible bases have been added and determined to be violating the parameters, the subsequence is also added to the VP list
   C) Once the sequence passes II.B, it is analyzed for other parameters defined in Section I
     1) If analysis in II.C demonstrates parameter violation, it is added to the VP list
   D) Once the sequence passes II.C, its complement is analyzed for other parameters in Section I
     1) If analysis in II.D demonstrates parameter violation, it is added to the VP list
   E) Add another random base and go to Step II.B until the length set in Section I is achieved II) Generate additional sequences (and complements) conforming to the parameters in Section I using the following steps:
   A) Following the procedure in Section II generate additional sequences
   B) Sequences added must pass both self-complement analysis as well as with existing sequences in the list previously generated
     1) Note that there is a user-controlled parameter to ignore interactions of those oligomers which are arbitrarily designated as being bound to a solid support
     2) The VP list quickly determines if possibilities are exhausted by keeping track of any subsequences which do not conform to parameters set in Section I In one embodiment, the invention comprises a method which includes the following steps:
   a) collecting user-controlled parameters;
   b) selecting a base at random to grow a first sequence;
   c) determining whether the first sequence is included on a VP list;
   d) removing the most recently added base of the first sequence, adding a different randomly selected base to the first sequence, and returning to step (c), if it is determined that the first sequence is on the VP list;
   e) analyzing the first sequence to determine whether it meets the user-controlled parameters if it is determined that the first sequence is not on the VP list;
   f) adding the first sequence to the VP list if it is determined that the first sequence violates the user-controlled parameters;
   g) adding a randomly selected base to the first sequence if it is determined that the first sequence does not violate the user-controlled parameters;
   h) repeating steps (b) through (g) if the first sequence is less than a user-specified length;

i) generating a complement to the first sequence if the first sequence is equal to the user-specified length;

j) determining whether the complement is included on a VP list;

k) adding the first sequence to the VP list if it is determined that the complement is on the VP list;

l) analyzing the complement to determine whether it meets the user-controlled parameters if it is determined that the complement is not on the VP list;

m) adding the first sequence to the VP list if it is determined that the complement violates the user-controlled parameters; and n) generating a second sequence using steps (b)-(m) to generate a second sequence.

The present invention also provides methods for validating the oligomer affinity pairs generated by the methods described above, which may be software-generated oligomer affinity pairs. One method for validating oligomer affinity pairs includes determining melting temperatures ($T_m$) for all possible duplexes, non-specific cross-interactions as well as self-interactions. Using the resulting data, the original software-generated set of oligomer affinity pairs can be then interrogated to reject the pairs that have failed to meet user-set criteria for the lowest acceptable margin for $T_m$ of specific duplexes and the highest acceptable margin for $T_m$ of non-specific duplexes. If necessary, the pairs that have met the criteria can be run through the design algorithm as a starting set to generate replacement pairs.

In another embodiment, the method for validating oligomer affinity pairs is a lateral flow test. In this method, one of the strands from each pair is bound in a specific arrangement on a lateral flow strip. The other strand from each pair, in combination with appropriate labeling strategy, is then brought into contact with the test strip one at the time to determine which solid phase-bound strands can interact with each solution phase strands.

The invention also contemplates the use of other methods, such as array based systems, to validate affinity pairs.

Software Calculations

% GC Calculation

The methods of producing oligomer affinity pairs provided by the present invention include the use of user-defined variable parameters to create stringency and stability among the oligomer affinity pairs. In one embodiment, the method uses user-controlled variable parameters to limit acceptable total % GC content for the user-specified length of the oligomer, as calculated using Equation 1, wherein $N_{Gi}$ is a guanosine at position i, $N_{Ci}$ is a cytidine at position i, and n is the user-specified length of oligomer.

$$\% \ GC_i = \frac{\sum_i (N_{Gi} + N_{Ci})}{n} \times 100\% \quad (1)$$

After each base addition at length i until total length n, the % $GC_i$ content is calculated and verified to be within the user defined parameters as represented by Equation 2.

$$\text{minimum } \% \ GC \leq \% \ GC_i \leq \text{maximum } \% \ GC \quad (2)$$

If % $GC_i$ is found to be outside of the parameters established in Equation 2, then the last added nucleotide is removed and neither G nor C is allowed to be added to the nucleotide.

$T_m$ Calculation

In one embodiment, the method uses user-controlled variable parameters to limit the final $T_m$ (melt temperature) of the oligomers. By establishing a user-controlled $T_m$ range, the software creates and lengthens an oligomer until the user-defined minimum $T_m$ is achieved. $T_m$ is calculated by adding the nearest neighbor values for enthalpy and entropy (Equations 3 and 4, respectively), and manipulating the sum of enthalpy ($\Delta H$) and entropy ($\Delta S$) at a given concentration (C) as in Equation 5, where R is the gas constant. Once the minimum $T_m$ is achieved, the $T_m$ at oligo length i is verified to be less than the user-defined maximum $T_m$; if true, the oligo is complete but if false and the last nucleotide added was a G or C, then A or T is added and the $T_m$ recalculated using Equations 3-5 and if Equation 6 is satisfied then the oligo is complete, and if not, the oligo is discarded.

$$\Delta H = \sum_i \Delta H_{NNi} \quad (3)$$

$$\Delta S = \sum_i \Delta S_{NNi} \quad (4)$$

$$\frac{1}{T_m} = \frac{R}{\Delta H} \ln \frac{C}{2} + \frac{\Delta S}{\Delta H} \quad (5)$$

$$\text{minimum } T_m \leq T_{mi} \leq \text{maximum } T_m \quad (6)$$

Method for Detecting a Nucleic Acid Target Sequence in a Lateral Flow Experiment In another embodiment, the present invention provides methods for detecting a nucleic acid target sequence. pRNA and pDNA affinity pairs may be designed and validated using the method described above, and the affinity pairs used in a lateral flow analysis to detect a target sequence. Lateral flow (immuno)assays are currently used for qualitative, semiquantitative and quantitative monitoring. Applications include tests of pathogens, drugs, hormones, metabolites in biomedical, veterinary, food, feed and environmental settings.

In one embodiment, the method for detecting a nucleic acid target sequence comprises the steps of:

a) designing a pRNA or pDNA affinity pair with a desired $T_m$ and specificity;

b) amplifying a target sequence with at least one chimeric primer, said chimeric primer comprising a pRNA or pDNA sequence of at least one member of said affinity pair;

c) capturing said amplified target on a solid support comprising an immobilized pRNA or DNA sequence complementary to said pRNA or chimeric pDNA sequence in said chimeric primer; and d) detecting said amplified target.

Example 1

Synthesis of pRNA and pDNA pRNAs are polymers composed of nucleoside monomeric units in which the natural ribofuranose sugar of RNA has been replaced with an isomeric ribopyranose sugar. The adjacent monomeric bases are connected to one another at their respective 2' and 4' positions through a phosphodiester linkage analogous to natural nucleic acids. The rigid conformation of the sugar rings and internucleoside linkages account for the remarkable stability of pRNA:pRNA duplexes. Methods for the preparation of pRNA are described in Eschenmoser et al., 1993, and U.S. Pat. No. 6,613,894, each of which is hereby incorporated herein by reference in its entirety.

pDNAs are polymers composed of nucleoside monomeric units in which the natural ribofuranose sugar of RNA has been replace with an isomeric 3'-deoxyribopyranose sugar. Similar to pRNAs, the adjacent monomeric bases are connected to one another at their respective 2' and 4' positions through a phosphodiester linkage analogous to natural nucleic acids. Methods for the preparation of pDNA were disclosed in U.S. Pat. No. 6,696,555, which is hereby incorporated herein by reference in its entirety.

pRNA and pDNA can be additionally modified with various functional groups such as biotin, fluorescent labels and spacers using appropriate DNA synthesis solid supports, phosphoramidites or other reactive intermediates. Examples of such reagents can be found in the Glen Research catalog.

Chimeric pRNA/DNA or pDNA/DNA

Chimeric pRNA/DNA or pDNA/DNA are polymers composed of both pRNA and DNA or pDNA and DNA monomeric units.

Chimeric polymers were assembled in blocks of pRNA, pDNA and DNA on a DNA synthesizer using properly protected pRNA, pDNA phosphoramidites described in U.S. Pat. No. 6,613,894 and U.S. Pat. No. 6,696,555 as well as standard DNA phosphoramidites. The blocks were connected either directly via a phosphodiester bond or via a spacer such spacer 9 using commercially available Spacer 9 phosphoramidite (Glen Research). pDNA-DNA chimeras were deprotected using standard concentrated ammonia deprotection conditions. pRNA-DNA chimeras were deprotected using gaseous ammonia (100-110 psi) at room temperature for 16 hrs to avoid pRNA degradation. All chimeric polymers were isolated using standard DMT-on purification followed by detritylation and DMT-off reverse phase HPLC purification.

Immobilization of pRNA and pDNA Affinity Pairs

Immobilization of a member of an affinity pair on nitrocellulose can be effected by various means. In the present example, a $T_{20}$ DNA tail was incorporated into the pRNA or pDNA oligomer to create a chimera which could be striped on the membrane then subjected to irradiation by ultraviolet light to cross-link the thymidine units on the $T_{20}$ tails, where the cross-linked products are immobilized. In other examples, oligomers have been conjugated to proteins, polystyrene particles, and other amine-functionalized polymers (aminodextran, poly-lysine, polyethyleneimine); these conjugates are striped on the nitrocellulose membrane and were held immobile within the nitrocellulose matrix by electrostatic forces when dried. Methods for conjugation of pRNA/pDNA to proteins and other amine-containing compounds are described in Hermanson, 1996.

Lateral Flow Detection

In order to detect hybridization of specific affinity pairs, nanoparticles doped with either a fluorescent or visible dye were employed. The particles were coated with a protein which binds biotin (eg, Neutravidin) and the bead was combined with a biotinylated oligomer complementary to a binding site on the nitrocellulose. Detection of nanoparticles with the visible dye can be achieved by the naked eye or by employing a color-saturation instrument. Detection of nanoparticles with the fluorescent dye can be achieved by ultraviolet illumination and detecting the fluorescent response either by the naked eye or by an instrument which detects the fluorescent emission. Europium chelate preparation and nanoparticle doping have been disclosed in US 2006/0166376 and U.S. Pat. No. 4,784,912.

Example 2

1. Synthesis and Purification

All pDNA, pRNA, pRNA-L-pDNA and pDNA-L-DNA oligonucleotides were synthesized on an ABI 3900 DNA synthesizer. In the case of some chimera oligomers, a linker compatible with synthesis was used. All oligomers and chimeras containing pRNA were deblocked with gaseous $NH_3$.

Unmodified, detritylated pDNA oligonucleotides were purified by reverse-phase HPLC using 5-40% acetonitrile in triethylammonium bicarbonate (pH 8) ramped over minutes. Pure product fractions were collected and evaporated to dryness. The resulting pellet was dissolved in water and quantified by UV-Vis spectrophotometry.

The $T_{20}$-tailed and biotinylated oligonucleotides were purified twice by reverse-phase HPLC. First, oligonucleotides with DMT-protecting group were purified using 5-40% acetonitrile in 100 mM triethylammonium bicarbonate buffer (ramped over 20 minutes), and the pure fractions were evaporated to dryness. The resulting DMT-on oligonucleotide was then deprotected by addition of 300 µL 80% acetic acid in water and allowed to react for 2 hours, then diluted to 3 mL volume using water and neutralized with 325 µL triethylamine. The detritylated product was then purified a second time by reverse-phase HPLC using 4-25% acetonitrile in 100 mM triethylammonium bicarbonate (ramped over 20 minutes) and the pure fractions were evaporated to dryness. The pellets were dissolved in water and quantified by UV-Vis spectrophotometry.

2. Melting Experiments

Unmodified oligonucleotide solutions were prepared at 5 µM in buffer (50 mM Tris-HCl, 200 mM NaCl, pH 7.0). The samples were denatured at 70° C. then cooled to 0° C. with a blanket of dry air. The temperature was raised by 1° C./min from ≤0 to 70° C. and the $T_m$ estimated at the midpoint between annealed and dissociated portions of the resulting absorbance curve.

3. Striping Experiment

Each of the biotinylated pDNA oligonucleotides were conjugated with NeutrAvidin-coated polystyrene nanoparticles doped with a fluorescent europium chelate by incubating for 15 minutes 200 µL 10 mM Tris-HCl (pH 8), 10 µL 5 µM biotinylated pDNA, and 20 µL 1% (w/v) NeutrAvidin-coated europium chelate-doped nanoparticles. Biotinylated DNA was then added to saturate the Neutravidin binding sites. 20 µL of the resulting nanoparticle suspensions were diluted with 775 µl buffer (50 mM Tris-HCl, 3% deoxycholate, 1% casein, 1% PEG8000, pH 8).

pDNA-T20 oligonucleotides were prepared as a 200 µM solution in 60 mM triethylammonium bicarbonate (pH 8) and striped using a BioDot striping instrument at a density of 0.6 µL/cm on Millipore HF pre-backed cards with a membrane length of 36 mm. Each of the 9 pDNA-T20 was striped at 3.3 mm distance from the next line. The dried membranes were irradiated with UV light for 7.5 minutes, fixed with an absorbent pad, and cut into 3-5 mm strips.

The striped membranes were immersed, upright, directly into a well containing 40 µL of the nanoparticle suspension, and after 15 minutes added 50 µL buffer (50 mM Tris-HCl, 200 mM NaCl. pH 7).

Example 3

This example demonstrates the preparation of the pDNA-Anchor striped card and pDNA fluorescent beads. It also describes a method for the lateral flow evaluation of 9 pDNA affinity ligand pairs.

pDNA—Anchor Conjugate Preparation pDNA oligonucleotides were synthesized on an ABI 3900 automated synthesizer using hexanol solid support. The 4' end of the pDNA was modified with an MMT-C12-amine moiety. The oligonucleotide was deprotected and cleaved from the solid support using ammonium hydroxide then concentrated to remove ammonia. The cleaved oligonucleotide was allowed to detritylate overnight in triethylammonium acetate (pH 5) buffer then purified by reverse phase HPLC using triethylammonium bicarbonate buffer. The fraction containing purified amine-modified pDNA was dried in a Speed Vac concentrator.

Purified amine-tailed pDNA was dissolved in DMSO and treated with phenylene diisothiocyanate (PDITC) and TEA. The crude PDITC-activated pDNA was precipitated using 2% $NaClO_4$ in acetone, centrifuged, and dried. The product pellet was dissolved in HPLC buffer and purified by reverse phase HPLC and then desalted.

Purified, desalted pDNA-PDITC was reacted with an "anchor," which may include proteins, peptides, aminodextrans, amine-containing beads, nucleic acids, or other molecules reactive towards pDNA-PDITC (Urdea et al., 1988; and Hermanson, 1996). Reaction conditions are typically pDNA-PDITC, an aqueous solution of the anchor, and sodium borate (pH 9) buffer; ratios of pDNA-PDITC to anchor can range from approximately 1:1000 to 1000:1, depending on the number of amine groups in the anchor. Reaction mixtures are purified by molecular weight cut-off (MWCO) filters subjected to centrifugation; MWCO filters are chosen as appropriate to the final molecular weight of the product. The retentate of the MWCO filter is washed with water or buffer and quantified by UV-Vis spectroscopy.

pDNA—Fluorescent Bead Preparation

Each of the biotinylated pDNA oligonucleotides were conjugated with NeutrAvidin-coated polystyrene nanoparticles doped with a fluorescent europium chelate by incubating for 15 minutes 200 µL 10 mM Tris-HCl (pH 8), 10 µL 5 µM biotinylated pDNA, and 20 µL 1% (w/v) NeutrAvidin-coated europium chelate-doped nanoparticles. Biotinylated DNA was then added to saturate the Neutravidin binding sites. 20 µL of the resulting nanoparticle suspensions were diluted with 775 µL buffer (50 mM Tris-HCl, 3% deoxycholate, 1% casein, 1% PEG8000, pH 8).

Negative Control beads were prepared using a DNA-biotin conjugate which saturated the available NeutrAvidin binding sites.

pDNA—Anchor Striped Card Preparation pDNA-PDITC—Anchor conjugates are dissolved in triethylammonium bicarbonate buffer at any nucleic acid concentration (typically 100 nM to 500 µM) and striped on a nitrocellulose membrane in any density range desired. Striped cards are dried by dessication or in a vacuum oven. Striped cards may be blocked with an appropriate blocking solution, if desired.

pDNA Cross-Reactivity Study

Each of the 9 pairs of pDNA-PDITC—Anchors shown in Table 1 was striped individually, then a 4 mm strip was screened using beads of each of the complementary 9-pairs. That is, for each of the pDNA sequences shown in Table 1, the dxay sequence was conjugated to an anchor then striped on the nitrocellulose; the dxay sequence was prepared as a fluorescent bead conjugate. For each dxay sequence, 10 strips were prepared and run with each of the 9 dxay bead (and one control) suspensions to check for non-complementary cross-reactivity.

TABLE 1 pDNA oligopolymers conjugated to an anchor for attachment to nitrocellulose.

| | |
|---|---|
| d9a8 | CTTCCATT |
| d9b8 | AATGGAAG |
| d14a8 | TCTCTCAT |
| d14b8 | ATGAGAGA |
| d15a8 | TGTAGTCA |
| d15b8 | TGACTACA |
| d17a9 | TTTTTTTTC |
| d17b9 | GAAAAAAAA |
| d18a8 | CAGATAGA |
| d18b8 | TCTATCTG |
| d20a8 | ACATCACA |
| d20b8 | TGTGATGT |
| d22a8 | GTAAGTTG |
| d22b8 | CAACTTAC |
| d23a8 | CAAGAATC |
| d23b8 | GATTCTTG |
| d24a8 | GAACAAAC |
| d24b8 | GTTTGTTC |

Results

Figure 4:
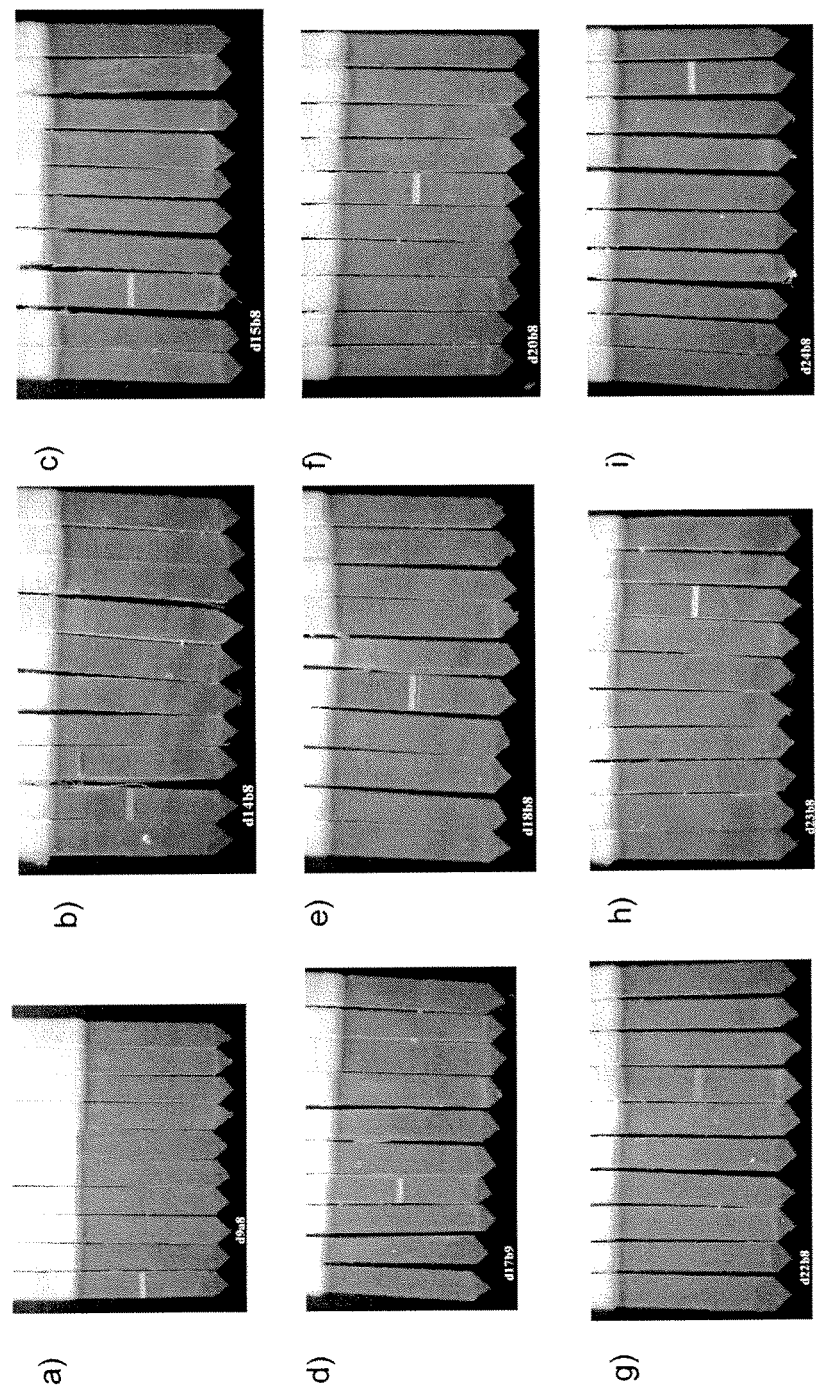
FIG. 4 illustrates the lateral flow analysis of 9 matched pDNA pairs from FIG. 3 that show no cross-interactions among the pairs.
Figure 5:
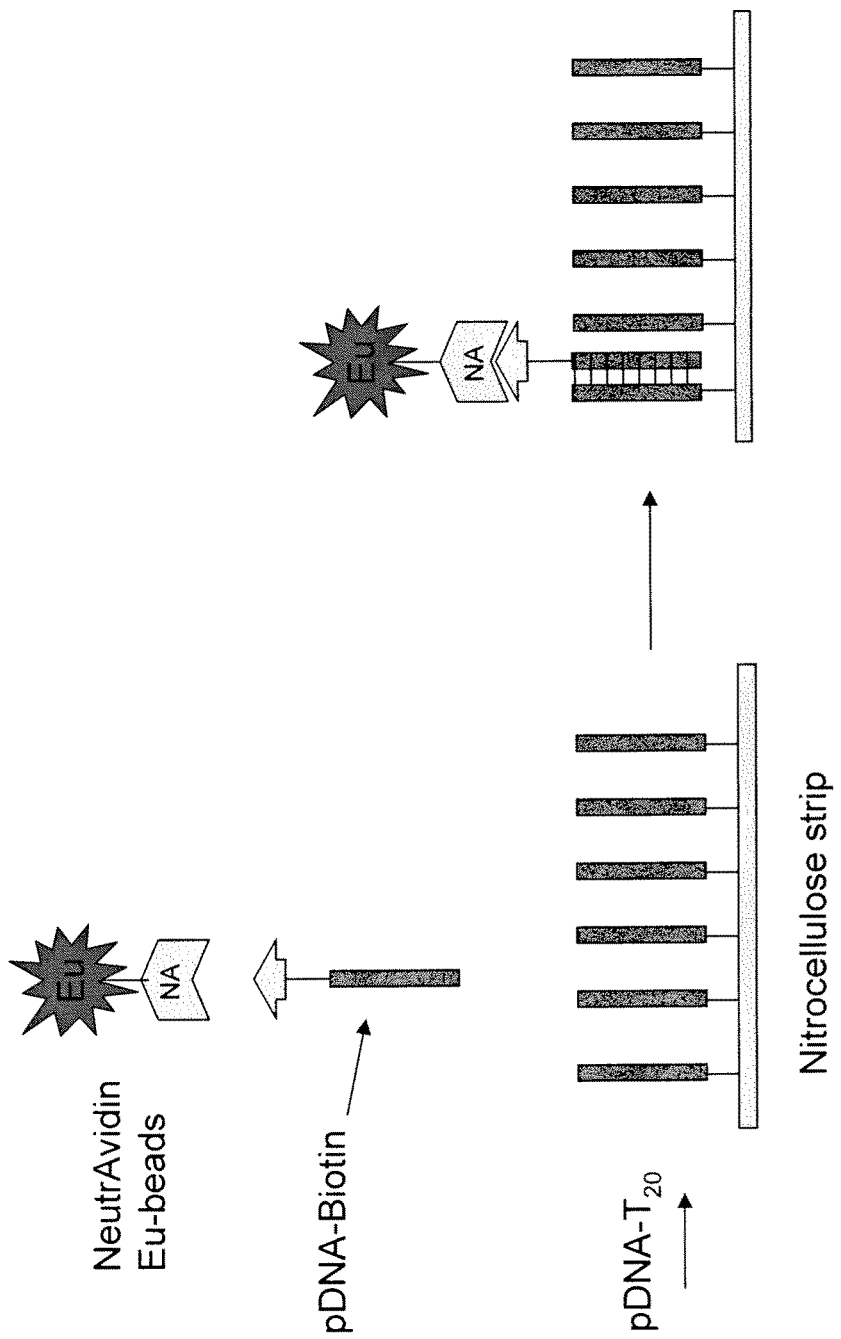
FIG. 5 illustrates a diagram of a model lateral flow test for evaluation of possible cross-interactions. The chimeric $T_{20}$-pDNA capture probe is UV-immobilized on a nitrocellulose strip. Data generated by this model system are shown in FIG. 7.
Figure 7:
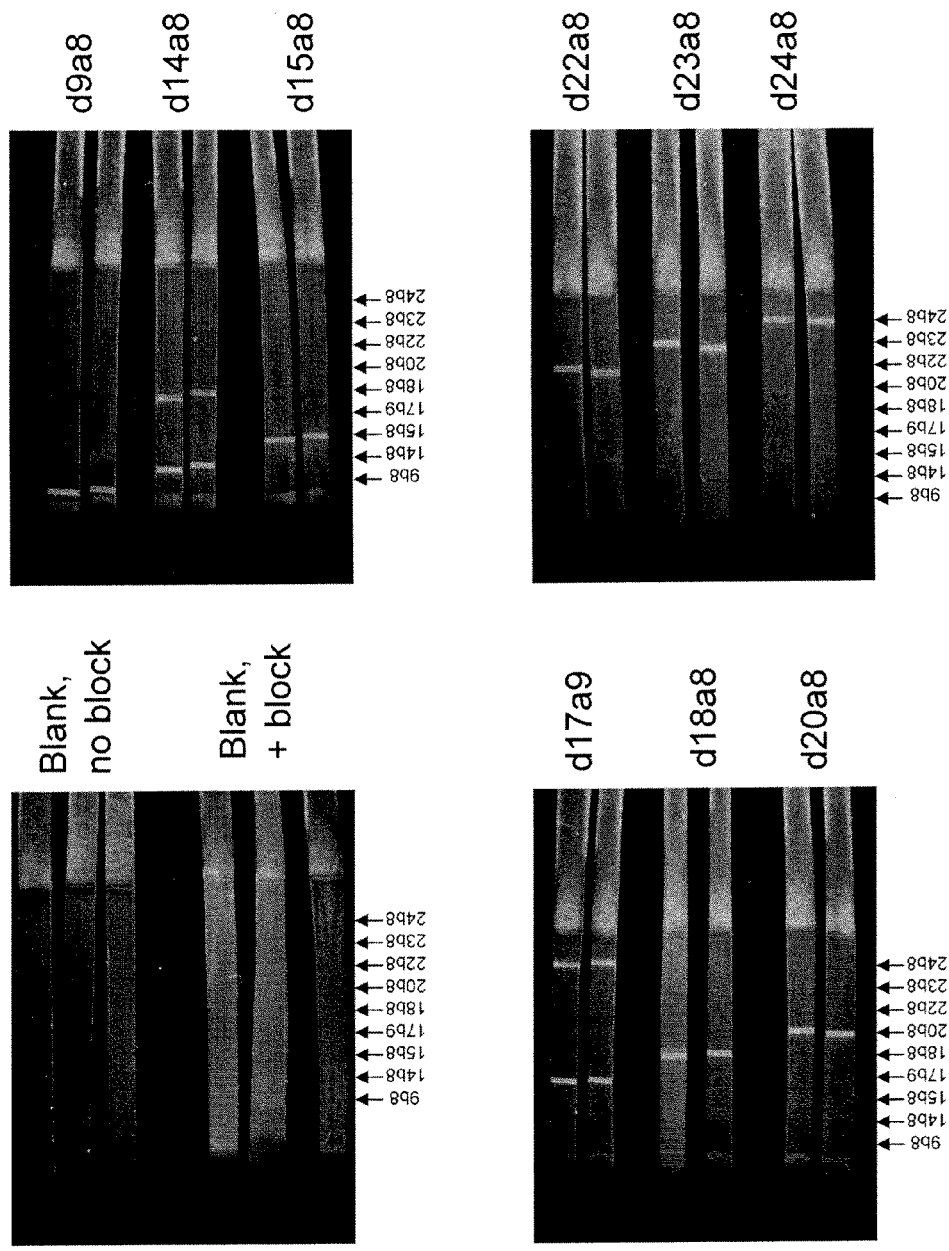
FIG. 7 illustrates the visual analysis of the lateral flow test results. The preparation of the strips and the protocol to run the lateral flow analysis is described in Example 3. Cross-interacting polymers can easily be identified by multiple bands on a strip.
Figure 9:
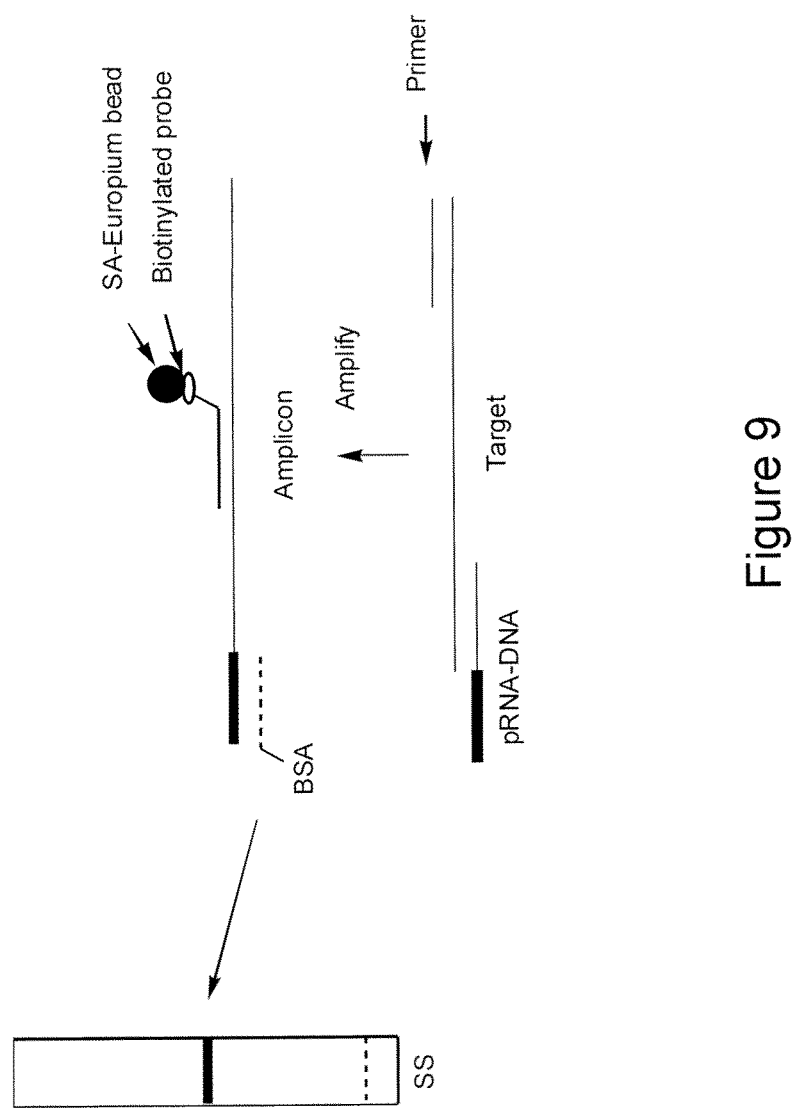
FIG. 9 schematically illustrates amplicon detection in a nucleic acid lateral flow (NALF) assay. Target is amplified where one primer is a chimera pRNA-DNA. The pRNA-labeled amplicon is captured on a lateral flow strip with a complementary pRNA attached to BSA protein. This pRNA-BSA was previously immobilized on the lateral flow strip. The amplified target is detected via a biotinylated probe-SA-europium bead complex.

FIG. 3 shows UV-illuminated photos, the ten strips were run with dxay beads as follows (left to right): a) d9a8; b) d14a8; c) d15a8; d) d17a9; e) d18a8; f) d20a8; g) d22a8; h) d23a8; i) d24a8, negative control. The fluorescent results are shown in FIG. 4 showing no significant cross reactivity among pairs.

Example 4

This example demonstrates a) the use of a chimera pRNA-pDNA; and b) the detection of a strand displacement amplified amplicon in a nucleic acid lateral flow (NALF) assay.

Strand Displacement Amplification

*Mycobacterium tuberculosis* (MTB) amplicon was obtained using isothermal Strand Displacement Amplification (SDA) method with the combination of the following primers:

L1:
[SEQ ID NO: 1]
GCATTATAGTACCTGTCT*CCTCAGC*ACTGAGATCCCCT

6a6-E001:
[SEQ ID NO: 2]
CAGTAG-(spacer9)-
TTGAATAGTCGGTTACTT*CCTCAGC*GCGTACTCGACC -continued Forward Bumper Primer 1:
[SEQ ID NO: 3]
CGCTGAACCGGAT Reverse Bumper Primer 1:
[SEQ ID NO: 4]
TGGACCCGCCAAC
*pRNA sequence is shown in bold
N.BbvC IA enzyme cleavage sites are underlined.

Amplifications were performed on samples containing *M. tuberculosis* target DNA (from strain SBRI10) in 10 μl final volume in a Rotor-Gene 3000 thermocycler (Corbett Research). Each sample contained 36 mM $K_2HPO_4$, pH 7.6, 3.75 mM $MgCl_2$, 0.25 mM each dNTPs (dATP, dGTP, dCTP and dTTP), 10 ng of human genomic DNA, 50 nM forward primer, 500 nM reverse primer, 50 nM each bumper primer, 4 U Bst DNA polymerase, 4 U BbvC1B (New England Biolabs) diluted in Diluent A (New England Biolabs). After addition of all the above components, including the two enzymes at room temperature, reaction tubes were placed directly in the thermocycler and were incubated at 45° C. for 45 min.

Real-Time Amplification Detection

Figure 10:
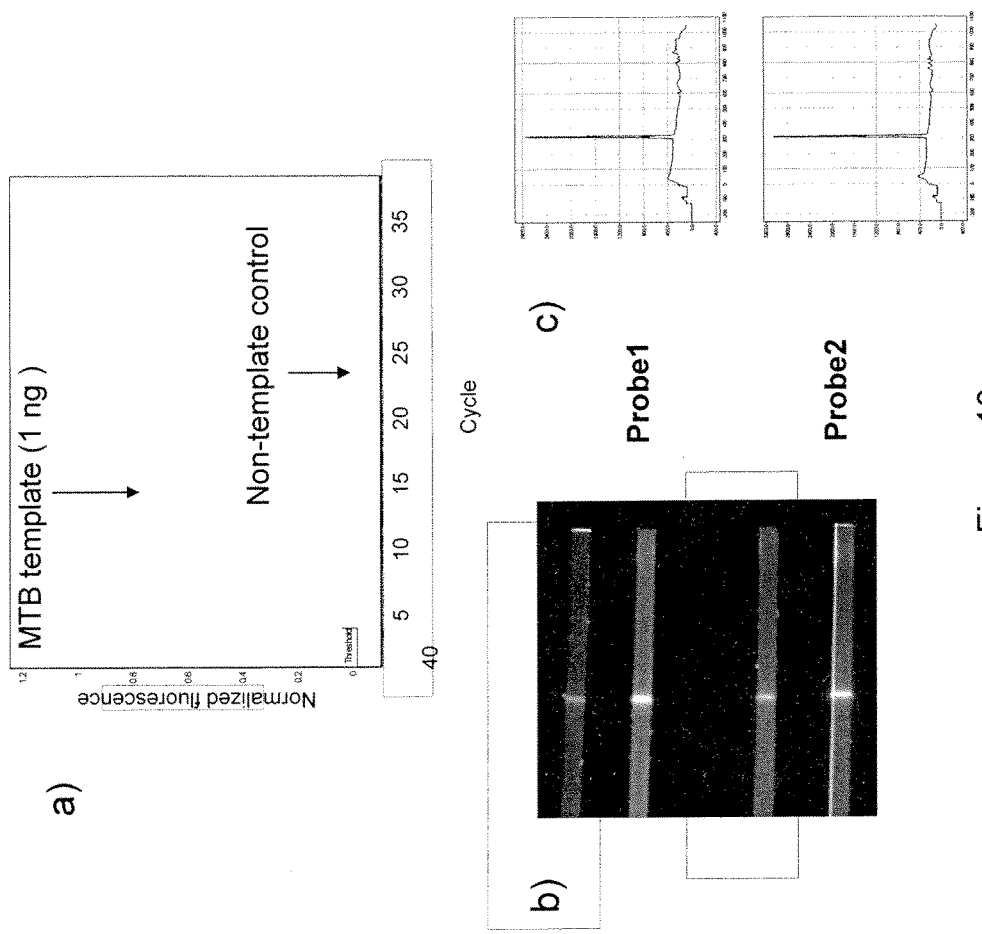
FIG. 10 illustrates a) the SDA amplification of *Mycoplasma tuberculosis* (MTB) template, b) the lateral flow detection of the amplified MTB target with a Europium-Streptavidin:biotin-probe complex and c) the fluorescent measurement of the NALF lateral flow strips using a Nanogen reader.

To ensure specific amplification, the resulting asymmetric amplicon was detected in a real time format using fluorescent detection probe MTB GG1 (TCCGTA*TGGTG-X-FAM, where A* is a super A base and X is an EndoIV linker; [SEQ ID NO:5-FAM]) and Rotor-Gene 3000 real time rotary analyzer (FIG. 10a). (U.S. Pat. No. 7,045,610; Kutyavin et al., 2006)

Immobilization of pRNAs on a Solid Support pRNA itself does not bind avidly to nitrocellulose. For irreversible binding of pRNA to nitrocellulose. $T_{20}$-pRNA chimeric oligonucleotide was used, sequence 6b6 4'-CTACTG. Reagents were spotted onto nitrocellulose HF135 (Whatman) in 0.25 μl volume, containing 25 pmol of pRNA (amount of each carrier varied). The reagents were allowed to dry for 1 hour. For covalent attachment of $T_{20}$, dry spotted nitrocellulose was cross-linked under UV light using a gel transilluminator (~300 nm) for 5 min. Nitrocellulose cards were cut into strips and used in NALF assay.

Amplicon Detection in Nucleic Acids Lateral Flow (NALF) Assay

For amplicon detection in NALF assay two biotinilated probes specific for non-coding strand of MTB amplicon were used.

[SEQ ID NO: 6]
Probe 1: Biotin-ATGGTGGATAACG

[SEQ ID NO: 7]
Probe 2: Biotin-GTGGATAACGTCTT*,
where T* is super T

Resulting amplicon and a hybridized probe were analyzed in dipstick lateral flow format. Biotinylated amplicons were incubated with Streptavidin-Europium beads for 30 min, diluted in 40 μl of NALF buffer (50 mM Tris, 3% sodium deoxycholate, 1% casein, 1% PEG 8000, pH=8.0) and tested in dipstick assay with HF135 nitrocellulose strips with immobilized 6b6 pRNA. 6b6 pRNA is complementary to the pRNA part of 6a6-E001 amplification primer. The results were visualized under UV light (FIG. 10b) and strips were read in Nanogen reader (FIG. 10c).

Example 5

This example demonstrates the detection of amplified target in a NALF format using colored beads.

Figure 11:
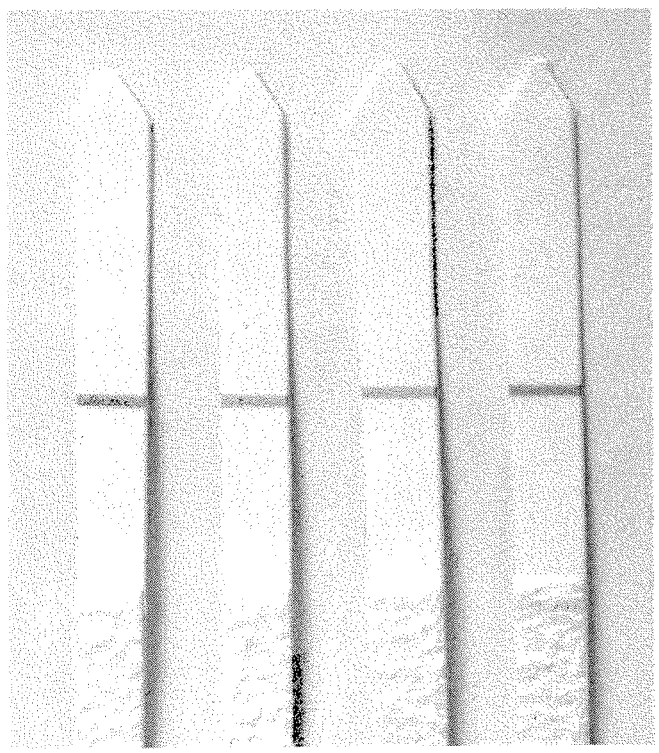
FIG. 11 illustrates detection on a 6b6 test strip in a NALF assay with complementary 6a6 pRNA bound to Neutravidin colored beads captured by the biotinylated amplicon-specific probe as described in Example 5.
Figure 12:
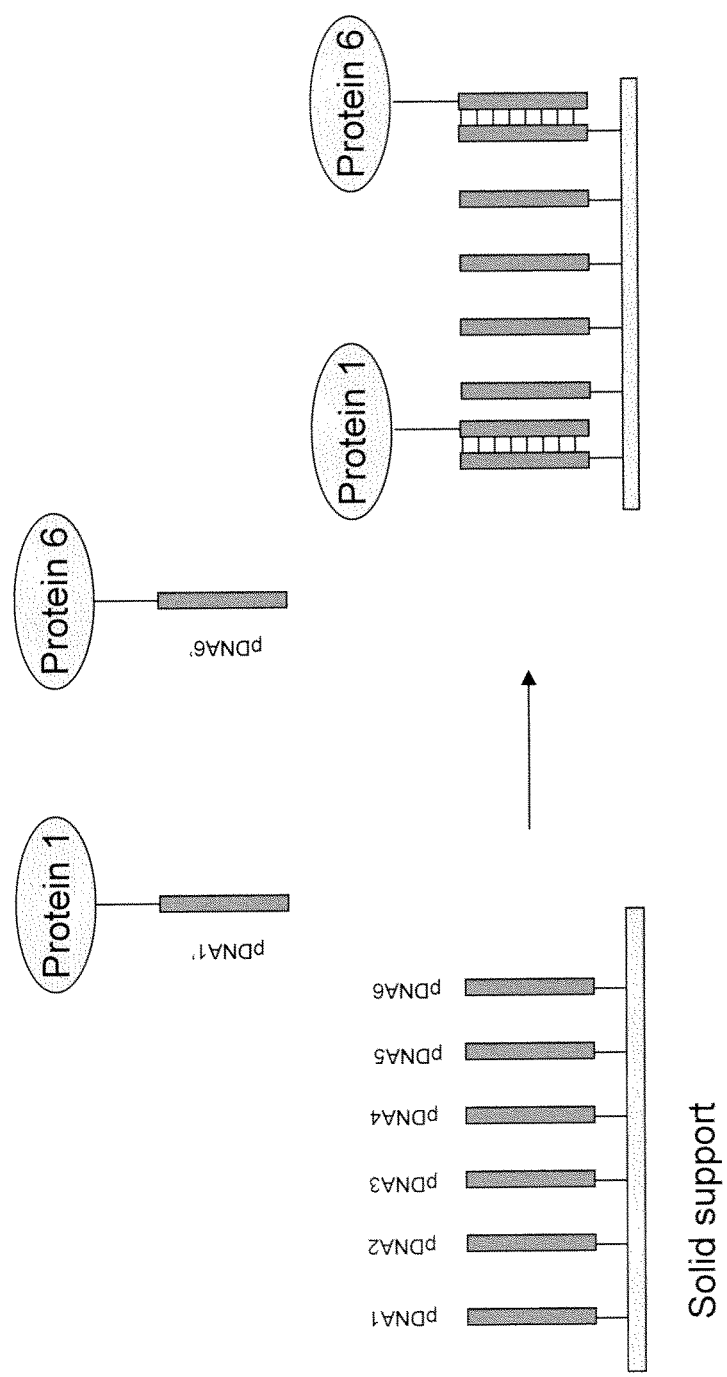
FIG. 12 illustrates a model for use of affinity oligomer ligand pairs to site-specifically immobilize more than one protein on a solid support. Immobilized proteins can be used, for example, in immunoassays, ligand screening and biomarker discovery.

Detection was performed similarly to the method described in Example 4 and lines were observed visually as shown in FIG. 11. Carboxyl-modified colored beads from Bangs Laboratories and Seradyn were used as shown in Table 2. The modification to make the carboxyl groups reactive to amine on Neutravidin is the same for each type of bead.

TABLE 2

Manufacturing description of colorimetric beads used.

| Color | Supplier | Catalog Number | Description |
| --- | --- | --- | --- |
| dark blue | Bangs Labs | DC02B | 330 nm 10% solids |
| black | Seradyn | 41400605020250 | 226 nm 2.5% solids |
| blue | Seradyn | 83100720020250 | 294 nm 2.5% solids |
| red | Seradyn | 83200720020250 | 294 nm 2.5% solids |

Neutravidin-Coupling Procedure:

15 mg beads were washed with 100 mM MES buffer (2-(N-morpholino)ethanesulfonic acid, pH 4-5) using centrifugation to isolate beads and resuspended with sonication. Beads were activated using a solution of 1.9 mg EDC (1-ethyl-3-(3-dimethylaminopropyl)carbodiimide) and 0.9 mg sulfo-NHS (N-hydroxysulfosuccinimide) in 1 mL 100 mM MES buffer for 1.5 h at room temperature. The reaction mixture was concentrated by centrifugation and the supernatant removed. To the resulting beads was added 750 μL of 0.667 mg/mL Neutravidin in 100 mM MES buffer and reacted overnight. The reaction mixture was washed five times with 2 mM Tris-HCl (pH 7).

Example 6

This example demonstrates the hybridization of pDNA with pRNA.

Melting experiments between pRNA and pDNA strands illustrate the relative stabilities of pRNA and pDNA duplexes. Experimental conditions used are 5 μM oligomers in various buffers with an initial elevated temperature to denature the duplexes, then cooled to 5° C. and ramped to 65 or 70° C. at a rate of 0.5° C./min. Oligomers consisted of duplexes of pXNA1-pXNA2, wherein pXNA1 is CAGTAG, and pXNA2 is CTACTG; X denotes pRNA or pDNA strands as detailed in Table 3.

Results in Table 3 show pure pRNA duplexes are substantially more stable than pDNA duplexes, with pRNA hybridizing to pDNA with intermediate stability.

TABLE 3

The $T_m$ of different pRNA and pDNA duplexes in three different buffers.

| Buffer Composition | pRNA-pRNA | pRNA-pDNA | pDNA-pRNA | pDNA-pDNA |
| --- | --- | --- | --- | --- |
| 50 mM Tris-HCl 200 mM NaCl | 41.9° C. | 37.4° C. | 36.3° C. | 29.5° C. |
| 50 mM NaCl 20 mM Na-cacodylate 0.5 mM $Na_2$-EDTA | 36.7° C. | 33.6° C. | 32.0° C. | 27.0° C. |
| 100 mM NaCl 10 mM $MgCl_2$ 10 mM Na-PIPES | 41.4° C. | 37.9° C. | 37.1° C. | 31.2° C. |

What is claimed:

1. A method of producing a set of oligomer affinity pairs for detection of targets using a lateral flow substrate, comprising the steps of:

a) acquiring:

i. a first set of user-controlled variables relating to stability of resulting oligomer affinity pairs comprising: a minimum percentage of guanine and cytosine (% GC minimum) within each oligomer affinity pair, and a maximum percentage of guanine and cytosine (% GC maximum) within each oligomer affinity pair, ii. a second set of one or more user-controlled variables relating to stringency of non-specific cross-interactions selected from the group consisting of: G-A mismatches counted as matches between oligomer affinity pairs, G-T mismatches counted as matches between oligomer affinity pairs, iii. a third set of one or more user-controlled variables relating to stringency of non-specific cross-interactions selected from the group consisting of: maximum consecutive matches in the oligomer affinity pairs, maximum consecutive matches of guanine and cytosine within consecutive matches in the oligomer affinity pairs, and minimum mismatches between maximum consecutive matches in the oligomer affinity pairs, and iv. user-selected sequence length;

b) initiating a cumulative list of non-compliant sequences, wherein sequences identified as inconsistent with the first set of user-controlled variables or third set of one or more user-controlled variables are referred to the cumulative list of non-compliant sequences;
c) generating a candidate sequence by adding a nucleic acid monomer to another nucleic acid monomer or to an existing sequence of nucleic acid monomers;
d) determining if the candidate sequence is identical to a sequence on the cumulative list of non-compliant sequences, and:
   i. if the candidate sequence is not identical to a sequence on the cumulative list of non-compliant sequences, proceeding to step (e), or
   ii. if sequences have not been referred to the cumulative list of non-compliant sequences, proceeding to step (e), or
   iii. if the candidate sequence is identical to a sequence on the cumulative list of non-compliant sequences, then removing the nucleic acid monomer most recently added to the candidate sequence, and returning to step (b), or
   iv. if the addition of each monomer A, C, G, and T results in a candidate sequence identical to a sequence on the cumulative list of non-compliant sequences, discarding the candidate sequence and returning to step (b);
e) generating a complementary sequence for the candidate sequence;
f) evaluating the candidate sequence and its complementary sequence for compliance with the first set of user-controlled variables, wherein said evaluating comprises:
   calculating a percentage of guanine and cytosine (% GC) for the candidate sequence or the complement sequence using the formula:

$$\% \text{ GC} = [\text{total number of guanine and cytosine in the candidate or complement sequence} \times 100\%]/\text{sequence length},$$

and evaluating if the % GC is within a range defined in the first set of user-controlled variables for % GC maximum and % GC minimum;
g) based on said evaluating, if the candidate sequence and its complementary sequence have a % GC within the range defined in the first set of user-controlled variables, proceeding to step (i); or h) based on said evaluating, if the candidate sequence or its complementary sequence have a % GC outside of the range defined in the first set of user-controlled variables, referring the candidate sequence and its complementary sequence to the cumulative list of non-compliant sequences, removing the nucleic acid monomer most recently added to the candidate sequence, and returning to step (b);
i) determining whether any oligomer affinity pairs have been previously produced for the set of oligomer affinity pairs and:
   i. if oligomer affinity pairs have not been produced for the set of oligomer affinity pairs and the candidate sequence and the complementary sequence have the user-selected sequence length, proceeding to step (n), or
   ii. if oligomer affinity pairs have not been produced for the set of oligomer affinity pairs and the candidate sequence and the complementary sequence have fewer monomers than the user-selected sequence length, returning to step (b), or
   iii. if oligomer affinity pairs have been previously produced for the set of oligomer affinity pairs, proceeding to step (j);
j) evaluating the candidate sequence and its complementary sequence against sequences of oligomers within the set of oligomer affinity pairs for compliance with the third set of one or more user-controlled variables, wherein said evaluating comprises:
   i. counting maximum consecutive matches using the second set of one or more user-controlled variables,
   ii. counting the consecutive matches of guanine and cytosine within consecutive matches,
   iii. counting the minimum mismatches between stretches of maximum consecutive matches, and
   iv. comparing the respective maximum and minimum values in the third set of one or more user-controlled variables to counted maximum consecutive matches, consecutive matches, and minimum mismatches;
k) based on said evaluating, if the candidate sequence and its complementary sequence have counted maximum consecutive matches, consecutive matches, and minimum mismatches within the respective maximum and minimum values of the third set of one or more user-controlled variables and the candidate sequence and the complementary sequence have the user-selected sequence length, proceeding to step (n); or
l) based on said evaluating, if the candidate sequence and its complementary sequence have counted maximum consecutive matches, consecutive matches, and minimum mismatches within the respective maximum and minimum values of the third set of one or more user-controlled variables and the candidate sequence and the complementary sequence have fewer monomers than the user-selected sequence length, returning to step (b); or
m) based on said evaluating, if the candidate sequence or its complementary sequence has counted maximum consecutive matches, consecutive matches, and minimum mismatches that are not within the respective maximum and minimum values of the third set of one or more user-controlled variables, performing the following:
   i. referring the candidate sequence and complementary sequence to the cumulative list of non-compliant sequences,
      removing the nucleic acid monomer most recently added to the candidate sequence, and returning to step (b), or
   ii. if the addition of each monomer A, C, G, and T results in a candidate sequence identical to a sequence on the cumulative list of non-compliant sequences, discarding the candidate sequence and returning to step (b), wherein all of the above steps are performed on a suitably programmed computer;
n) synthesizing a first oligomer having the candidate sequence and a second oligomer having the complementary sequence, wherein the first oligomer and the second oligomer constitute an oligomer affinity pair within an oligomer affinity pair set, wherein the first oligomer and the second oligomer are comprised of 3-deoxypyranosyl nucleic acid (pDNA) or pyranosyl nucleic acid (pRNA), and wherein the first oligomer and the second oligomer preferentially hybridize to each other and not to naturally occurring DNA or RNA;
o) repeating steps (b) through (n) to produce additional oligomer affinity pairs comprising additional first oligomers and additional second oligomers having sequences in compliance with the first set of user-controlled variables and third set of one or more user-controlled variables;
p) attaching first oligomers of the first oligomer affinity pair and the additional oligomer affinity pairs to a lateral flow substrate, wherein the lateral flow substrate is selected from the group consisting of membranes, microfluidic channels, microspheres, magnetic beads, color beads, microarrays, microtiterplates, microchips, nylon surfaces, gold surfaces, polystyrene surfaces, and nanoparticles;
q) exposing the lateral flow substrate to target complexes, wherein each target complex comprises a target oligomer having a target oligomer sequence selected from at least a portion of the second oligomers of the oligomer affinity pairs, wherein the target oligomers of the target complexes hybridize to corresponding first oligomers attached to the lateral flow substrate, and wherein the oligomers of each oligomer affinity pair preferentially hybridize to each other; and
r) detecting a target by detecting hybridization of the target oligomer to its corresponding first oligomer.

2. The method of claim 1, further comprising the step of: experimentally validating at least one oligomer affinity pair.

3. The method of claim 2, wherein the oligomer affinity pair is experimentally validated by determining melting temperatures for the oligomer affinity pair.

4. The method of claim 2, wherein the oligomer affinity pair is experimentally validated by performing a lateral flow test.

5. The method of claim 1, wherein the step of exposing the lateral flow substrate to target complexes further comprises amplifying the target oligomer with at least one chimeric primer, said chimeric primer comprising a sequence selected from the second oligomers of the first oligomer affinity pair and the additional oligomer affinity pairs.

6. The method of claim 1, wherein oligomer affinity pairs in the set of oligomer affinity pairs comprise:
a first oligomer having a sequence of CTTCCATT and a second oligomer having a sequence of AATGGAAG; or
a first oligomer having a sequence of TCTCTCAT and a second oligomer having a sequence of ATGAGAGA; or
a first oligomer having a sequence of TGTAGTCA and a second oligomer having a sequence of TGACTACA; or
a first oligomer having a sequence of TTTTTTTC and a second oligomer having a sequence of GAAAAAAA; or
a first oligomer having a sequence of CAGATAGA and a second oligomer having a sequence of TCTATCTG; or
a first oligomer having a sequence of ACATCACA and a second oligomer having a sequence of TGTGATGT; or
a first oligomer having a sequence of GTAAGTTG and a second oligomer having a sequence of CAACTTAC; or
a first oligomer having a sequence of CAAGAATC and a second oligomer having a sequence of GATTCTTG; or
a first oligomer having a sequence of GAACAAAC and a second oligomer having a sequence of GTTTGTTC.

7. A method of producing a set of oligomer affinity pairs for detection of targets using a lateral flow substrate, comprising the steps of:
a) acquiring:
i. a first set of user-controlled variables relating to stability of resulting oligomer affinity pairs comprising: a minimum predicted duplex melting temperature within each oligomer affinity pair, and a maximum predicted duplex melting temperature within each oligomer affinity pair,
ii. a second set of one or more user-controlled variables relating to stringency of non-specific cross-interactions selected from the group consisting of: G-A mismatches counted as matches between oligomer affinity pairs, G-T mismatches counted as matches between oligomer affinity pairs,
iii. a third set of one or more user-controlled variables relating to stringency of non-specific cross-interactions selected from the group consisting of: maximum consecutive matches in the oligomer affinity pairs, maximum consecutive matches of guanine and cytosine within consecutive matches in the oligomer affinity pairs, and minimum mismatches between maximum consecutive matches in the oligomer affinity pairs, and
iv. user-selected sequence length;
b) initiating a cumulative list of non-compliant sequences, wherein sequences identified as inconsistent with the first set of user-controlled variables or third set of one or more user-controlled variables are referred to the cumulative list of non-compliant sequences;
c) generating a candidate sequence by adding a nucleic acid monomer to another nucleic acid monomer or to an existing sequence of nucleic acid monomers;
d) determining if the candidate sequence is identical to a sequence on the cumulative list of non-compliant sequences, and:
i. if the candidate sequence is not identical to a sequence on the cumulative list of non-compliant sequences, proceeding to step (e), or
ii. if sequences have not been referred to the cumulative list of non-compliant sequences. proceeding to step (e). or
iii. if the candidate sequence is identical to a sequence on the cumulative list of non-compliant sequences, then removing the nucleic acid monomer most recently added to the candidate sequence, and returning to step (b), or
iii. if the addition of each monomer A, C, G, and T results in a candidate sequence identical to a sequence on the cumulative list of non-compliant sequences, discarding the candidate sequence and returning to step (b);
e) generating a complementary sequence for the candidate sequence;
f) evaluating the candidate sequence and its complementary sequence for compliance with the first set of user-controlled variables, wherein said evaluating comprises:
calculating a predicted melt temperature (Tm) for the candidate sequence or the complement sequence using the formula:

$$1/Tm = R/\Delta H\ \ln(C/2) + \Delta S/\Delta H,$$

wherein R is 8.3145 J/mol K, $\Delta H$ is a sum of nearest neighbor values for enthalpy in the candidate sequence. $\Delta S$ is a sum of nearest neighbor values for entropy in the candidate sequence, and C is the selected concentration, and comparing the predicted Tm against the range defined by the first set of user-controlled variables;
g) based on said evaluating, if the candidate sequence and its complementary sequence have a predicted Tm within the range defined in the first set of user-controlled variables, proceeding to step (i); or
h) based on said evaluating, if the candidate sequence or its complementary sequence have a predicted Tm outside of the range defined in the first set of user-controlled variables, referring the candidate sequence and its complementary sequence to the cumulative list of non-compliant sequences, removing the nucleic acid monomer most recently added to the candidate sequence, and returning to step (b);
i) determining whether any oligomer affinity pairs have been previously produced for the set of oligomer affinity pairs and:
  i. if oligomer affinity pairs have not been produced for the set of oligomer affinity pairs and the candidate sequence and the complementary sequence have the user-selected sequence length, proceeding to step (n), or
  ii. if oligomer affinity pairs have not been produced for the set of oligomer affinity pairs and the candidate sequence and the complementary sequence have fewer monomers than the user-selected sequence length, returning to step (b), or
  iii. if oligomer affinity pairs have been previously produced for the set of oligomer affinity pairs, proceeding to step (j);
j) evaluating the candidate sequence and its complementary sequence against sequences of oligomers within the set of oligomer affinity pairs for compliance with the third set of one or more user-controlled variables, wherein said evaluating comprises:
  i. counting maximum consecutive matches using the second set of one or more user-controlled variables,
  ii. counting the consecutive matches of guanine and cytosine within consecutive matches,
  iii. counting the minimum mismatches between stretches of maximum consecutive matches, and
  iv. comparing the respective maximum and minimum values in the third set of one or more user-controlled variables to counted maximum consecutive matches, consecutive matches, and minimum mismatches;
k) based on said evaluating, if the candidate sequence and its complementary sequence have counted maximum consecutive matches, consecutive matches, and minimum mismatches within the respective maximum and minimum values of the third set of one or more user-controlled variables and the candidate sequence and the complementary sequence have the user-selected sequence length, proceeding to step (n); or
l) based on said evaluating, if the candidate sequence and its complementary sequence have counted maximum consecutive matches, consecutive matches, and minimum mismatches within the respective maximum and minimum values of the third set of one or more user-controlled variables and the candidate sequence and the complementary sequence have fewer monomers than the user-selected sequence length, returning to step (b); or
m) based on said evaluating, if the candidate sequence or its complementary sequence has counted maximum consecutive matches, consecutive matches, and minimum mismatches that are not within the respective maximum and minimum values of the third set of one or more user-controlled variables, performing the following:
  i. adding referring the candidate sequence and complementary sequence to the cumulative list of non-compliant sequences, removing the nucleic acid monomer most recently added to the candidate sequence, and returning to step (b), or
  ii. if the addition of each monomer A, C, G, and T results in a candidate sequence identical to a sequence on the cumulative list of non-compliant sequences, discarding the candidate sequence and returning to step (b), wherein all of the above steps are performed on a suitably programmed computer;
n) synthesizing a first oligomer having the candidate sequence and a second oligomer having the complementary sequence, wherein the first oligomer and the second oligomer constitute an oligomer affinity pair within an oligomer affinity pair set, wherein the first oligomer and the second oligomer are comprised of 3-deoxypyranosyl nucleic acid (pDNA) or pyranosyl nucleic acid (pRNA), and wherein the first oligomer and the second oligomer preferentially hybridize to each other and not to naturally occurring DNA or RNA;
o) repeating steps (b) through (n) to produce additional oligomer affinity pairs comprising additional first oligomers and additional second oligomers having sequences in compliance with the first set of user-controlled variables and third set of one or more user-controlled variables;
p) attaching first oligomers of the first oligomer affinity pair and the additional oligomer affinity pairs to a lateral flow substrate, wherein the lateral flow substrate is selected from the group consisting of membranes, microfluidic channels, microspheres, magnetic beads, color beads, microarrays, microtiterplates, microchips, nylon surfaces, gold surfaces, polystyrene surfaces, and nanoparticles;
q) exposing the lateral flow substrate to target complexes, wherein each target complex comprises a target oligomer having a target oligomer sequence selected from at least a portion of the second oligomers of the oligomer affinity pairs, wherein the target oligomers of the target complexes hybridize to corresponding first oligomers attached to the lateral flow substrate, and wherein the oligomers of each oligomer affinity pair preferentially hybridize to each other; and
r) detecting a target by detecting hybridization of the target oligomer to its corresponding first oligomer.

8. The method of claim 7, further comprising the step of: experimentally validating at least one oligomer affinity pair.

9. The method of claim 8, wherein the oligomer affinity pair is experimentally validated by determining melting temperatures for the oligomer affinity pair.

10. The method of claim 8, wherein the oligomer affinity pair is experimentally validated by performing a lateral flow test.

11. The method of claim 7, wherein the step of exposing the lateral flow substrate to target complexes further comprises amplifying the target oligomer with at least one chimeric primer, said chimeric primer comprising a sequence selected from the second oligomers of the first oligomer affinity pair and the additional oligomer affinity pairs.

12. The method of claim 7, wherein oligomer affinity pairs in the set of oligomer affinity pairs comprise:

a first oligomer having a sequence of CTTCCATT and a second oligomer having a sequence of AATGGAAG; or a first oligomer having a sequence of TCTCTCAT and a second oligomer having a sequence of ATGAGAGA; or a first oligomer having a sequence of TGTAGTCA and a second oligomer having a sequence of TGACTACA; or a first oligomer having a sequence of TTTTTTTTC and a second oligomer having a sequence of GAAAAAAAA; or a first oligomer having a sequence of CAGATAGA and a second oligomer having a sequence of TCTATCTG; or a first oligomer having a sequence of ACATCACA and a second oligomer having a sequence of TGTGATGT; or a first oligomer having a sequence of GTAAGTTG and a second oligomer having a sequence of CAACTTAC; or a first oligomer having a sequence of CAAGAATC and a second oligomer having a sequence of GATTCTTG; or a first oligomer having a sequence of GAACAAAC and a second oligomer having a sequence of GTTTGTTC.

* * * * *